US006420455B1

(12) United States Patent
Landgrebe et al.

(10) Patent No.: US 6,420,455 B1
(45) Date of Patent: Jul. 16, 2002

(54) ANTIMICROBIAL COMPOSITION CONTAINING PHOTOSENSITIZERS ARTICLES, AND METHODS OF USE

(75) Inventors: Kevin D. Landgrebe, Woodbury; John J. Stofko; Sheila A. Tesch, both of St. Paul; John C. Loperfido, Stillwater, all of MN (US); David J. Hastings, London (CA); Thomas J. Packard, Somerset, WI (US); Matthew T. Scholz, Woodbury, MN (US); Linda K. Olson; Kaveh Pournoor, both of St. Paul, MN (US); Monserrat R. Lalonde, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/336,396

(22) Filed: Jun. 18, 1999

(51) Int. Cl.$^7$ ................................................ C08K 5/06

(52) U.S. Cl. ................................................... 523/122

(58) Field of Search ........................................ 523/122

(56) References Cited

U.S. PATENT DOCUMENTS

| | | | |
|---|---|---|---|
| 4,440,258 A | | 4/1984 | Packard |
| 4,638,043 A | * | 1/1987 | Szycher ........................ 528/75 |
| 4,885,332 A | * | 12/1989 | Bilkadi ........................ 524/714 |
| 4,888,175 A | | 12/1989 | Burton, Jr. et al. |
| 4,908,381 A | | 3/1990 | Greenwald et al. |
| 4,921,589 A | | 5/1990 | Yates et al. |
| 4,986,921 A | | 1/1991 | Yates et al. |
| 5,104,649 A | | 4/1992 | Jansson et al. |
| 5,180,605 A | | 1/1993 | Milner |
| 5,236,703 A | | 8/1993 | Usala |
| 5,238,749 A | | 8/1993 | Cueman et al. |
| 5,340,614 A | | 8/1994 | Perman et al. |
| 5,452,792 A | | 9/1995 | Zautke et al. |
| 5,532,290 A | | 7/1996 | Newington et al. |
| 5,532,291 A | | 7/1996 | Wright et al. |
| 5,585,407 A | | 12/1996 | Patel et al. |
| 5,626,968 A | * | 5/1997 | Priou ........................ 428/447 |
| 5,639,546 A | * | 6/1997 | Bilkadi ........................ 428/331 |
| 5,641,464 A | | 6/1997 | Briggs, III et al. |
| 5,780,043 A | | 7/1998 | Dane et al. |
| 5,786,198 A | | 7/1998 | Kraus et al. |
| 5,830,526 A | | 11/1998 | Wilson et al. |
| 5,967,714 A | * | 10/1999 | Ottersbach ............... 408/424.2 |
| 6,096,800 A | * | 8/2000 | Ottersbach ................. 523/122 |
| 6,239,048 B1 | | 5/2001 | Wilson et al. |

FOREIGN PATENT DOCUMENTS

| | | |
|---|---|---|
| GB | 2 262 468 A | 6/1993 |
| JP | 56-39004 | 4/1981 |
| WO | WO 93/00815 | 1/1993 |
| WO | WO 94/02022 | 2/1994 |
| WO | WO 94/13748 | 6/1994 |
| WO | WO 98/20094 | 5/1998 |
| WO | WO 99/37154 | 7/1999 |
| WO | WO 99/49823 | 10/1999 |

OTHER PUBLICATIONS

Cuny et al., "Photoactivated Virucidal Properties of Tridentate 2,2'–dihydroxyazobenzene and 2–salicylideneaminophenol Platinum Pyridine Complexes," *Bioorg. Med. Chem. Lett.*, 9:237–240 (1999).
Smith et al., "The Bacteriostatic Action of Rose Bengal in Media used for Plate Counts of Soil Fungi," *Soil Science*, 58(1):467–471 (1944).
Bezman et al., "Photodynamic Inactivation of *E. Coli* By Rose Bengal Immobilized On Polystyrene Beads," *Photochemistry and Photobiology* 28:325–329 (1978).
Dahl et al., "Pure Singlet Oxygen Cytotoxicity for Bacteria," *Photochemistry and Photobiology* 46:345–352 (1987).
Facchin et al., "Phosphazene–Bound Rose Bengal: A Novel Photosensitizer for Singlet Oxygen Generation," *Journal of Inorganic and Organometallic Polymers* 1:389–395 (1991).
Heitz et al., "Development of Photoactivated Compounds as Pesticides," *Light–Activated Pesticides, ACS Symp. Ser.* 339:1–21, Chapter 1 (1987).
Ikeda et al., "Self–Sterilizing Materials. 2. Evaluation of Surface Antibacterial Activity," *Journal of Bioactive and Compatible Polymers* 1:301–308 (1986).
Judd et al., *Color in Business, Science, and Industry*, 2nd ed., published by John Wiley and Sons, Inc., New York, p. 295–296 (1963).
Kanazawa et al., "Polymeric Phosphonium Salts as a Novel Class of Cationic Biocides. VI. Antibacterial Activity of Fibers Surface–Treated with Phosphonium Salts Containing Trimethoxysilane Groups," *Journal of Applied Polymer Science*, 52 641–647 (1994).
Kenawy et al., "Biologically active polymers: synthesis and antimicrobial activity of modified glycidyl methacrylate polymers having a quaternary ammonium and phosphonium groups," *Journal of Controlled Release* 50:145–152 (1998).
Lenard et al., "Photoinactivation of Influenza Virus Fusion and Infectivity by Rose Bengal," *Photochemistry and Photobiology* 58:527–531 (1993).
Neckers, "Polymeric Photosensitizers," *Polymeric Reagents and Catalysts*, American Chemical Society, 107–131, Chapter 6 (1986).
Nilsson et al., "Some Useful Heterogeneous Systems for Photosensitized Generation of Singlet Oxygen," *Photochemistry and Photobiology* 19:181–184 (1974).
Schaap et al., "Photooxygenations in Aqueous Solution with a Hydrophilic Polymer–Immobilized Photosensitizer," *Journal of the American Chemical Society* 101:4016–4017 (1979).
Schaap et al., "Polymer–Based Sensitizers for Photooxidations. II" *Journal of American Chemical Society*, 97:13 (1975).
Tseng et al., "Characterization of Photodynamic Actions of Rose Bengal on Cultured Cells," *Investigative Ophthalmology & Visual Science* 35:3295–3307 (1994)
*Dictionary of Organic Compounds*, Fifth Edition, vol. 5, Chapman and Hall, New York/London/Toronto, Title page and p. 5739.

* cited by examiner

Primary Examiner—Paul R. Michl
(74) *Attorney, Agent, or Firm*—Yen Tong Florczak

(57) ABSTRACT

Polymer compositions and articles incorporating them are provided that possess antimicrobial activity, preferably in both the light and the dark. Such compositions include one or more polymers and one or more photosensitizers.

50 Claims, 1 Drawing Sheet

ANTIMICROBIAL COMPOSITION CONTAINING PHOTOSENSITIZERS ARTICLES, AND METHODS OF USE

FIELD OF THE INVENTION

This invention relates to the field of microbiology, and in particular to antimicrobial compositions, particularly to antimicrobial compositions that yield polymeric films, coatings, or shaped articles having prolonged antimicrobial activity, particularly in both the light and the dark.

BACKGROUND

The potential for the presence of pathogenic bacteria and viruses in biological fluids such as saliva, tears, blood, and lymph is of significant concern as is the potential for the transfer of such microorganisms to the surfaces of medical devices (and vice versa). For these reasons, methods for minimizing the transmission of pathogens in the home and in hospitals, as well no as in daycare centers, are important.

Microorganisms (e.g., viruses, bacteria, fungi) can be killed or rendered static by a number of physical and chemical methods. Physical methods include heat and radiation. There are a number of chemicals that have been used to limit viral, fungal, and bacterial growth. Examples include alcohols (usually as 70% by volume aqueous ethyl- or isopropyl alcohol), phenol (carbolic acid) and phenol derivatives such as hexachlorophene, formaldehyde, glutaraldehyde, ethylene oxide, ether, detergents, chlorhexidine gluconate, heavy metals such as silver, copper, and mercury, organic compounds of mercury such as mercurochrome, oxidizing agents such as hydrogen peroxide, iodine, hypochlorite, and chlorine. A number of antiviral agents are also known, including amantadine, nucleoside analogs such as AZT, aciclovir, ganciclovir, and vidarabine.

Antibiotics, such as bacitracin, the cephalosporins, cycloserine, the penicillins, vancomycin, chloramphenicol, the erythromycins, the tetracyclines, the sulfonamides, and the aminoglycosides (such as streptomycin, neomycin, and gentamycin), have traditionally been defined as chemicals made by microorganisms that kill bacteria. Antibiotics have no effect on viruses.

Such treatment methods are neither permanent nor continuous. thus repeated treatments may be needed. Compositions intended for imparting a continuously antimicrobial, self-disinfectinig property to surfaces or liquids have been disclosed, most of which involve covalent attachment of an antimicrobial moiety to a polymer or mixture of an antimicrobial agent with a polymer to impart controlled release of the antimicrobial agent.

Generally, known compositions intended for imparting continuous antimicrobial, self-disinfecting activity require intimate contact of the antimicrobial agent or antimicrobial moiety with a given bacterium, fungus, or virus. Since surfaces, in particular, inevitably become soiled, potentially precluding intimate contact of an antimicrobial agent or moiety with the contaminating microbe, it would be of potential benefit to have a method for imparting continuous antimicrobial, self-disinfecting activity at-a-distance, Such a method was disclosed by Dahl et al., *Photochemistry and Photobiology*, 46, 3, 345–352 (1987) in which *E. coli* were separated from a surface by about 0.65 mm, wherein the surface included rose bengal. The method involved irradiating the rose bengal using visible light. The antimicrobial activity at-a-distance was ascribed to the diffusion of toxic singlet oxygen through air to the bacteria. Singlet oxygen itself is known to be generated by irradiation of rose bengal and other so-called triplet sensitizers.

Singlet oxygen is generated in neutrophils and macrophages for use in killing microorganisms. Superoxide dismutases, catalases, and peroxidases are defenses against radical- and reduced-oxygen species, but are not effective against singlet oxygen. A few microorganisms, such as Cercospora, are inherently resistant to singlet oxygen, and Gram-positive bacteria are generally more easily killed by singlet oxygen than Gram-negative bacteria. Enveloped viruses are inactivated by singlet oxygen more readily than nonenveloped viruses. It is notable that not a single documented case of acquired resistance by a bacterium, fungus, or virus to singlet oxygen is known.

The "photodynamic effect" is the term used to describe destruction of cells and microbes by triplet-sensitizers in the presence of light. Under conditions where oxygen concentration is high and there are no reducing agents present, singlet oxygen is believed to be the destructive agent. This is the predominant mechanism (the so-called Type II mechanism) for cell destruction in cases where the photosensitizer cannot enter the cell. The Type II mechanism is known to be the predominant means of phototoxicity to *E. coli* for the xanthene dyes, such as rose bengal, for example, which upon irradiation generates reactive oxygen species. 80% of which are singlet oxygen, and 20% of which are superoxide radical anions. For photosensitizers that can pass through the lipid bilayer membrane into the interior of the cell where reducing agent concentrations, such as NADPH and glutathione, are high, the so-called Type I mechanism has been determined to be the predominant one leading to cell destruction. This mechanism involves, ultimately, the formation of a photosensitizer free radical and hydrogen peroxide, hydroxyl radical, and superoxide radical anion.

Some effort has been directed toward utilization of a combination of light and triplet-sensitizers (e.g., phthalocyanine, porphyrin hypericin, and rose bengal) for killing bacteria and fungi and for inactivating viruses. For example, photoinactivation of influenza virus by rose bengal and light was disclosed by Lenard et al., *Photochemistry and Photobiology*, 58, 527–531 (1993). Also, International Patent Application No. WO 94/02022 discloses improved germicidal compositions utilizing rose bengal in photodynamic killing of microorganisms on surfaces.

As stated above, chemical attachment (e.g., covalent or ionic) of photosensitizers to, or physical mixing of photosensitizers with, polymers has been of significant interest to workers in this field. Incorporation of dyes, such as xanthene dyes like rose bengal, into polymer matrices has been described in U.S. Pat. No. 5,830,526 (Wilson et al.), for example, which describes a woven or nonwoven fabric bound with a non-leachable light-activated dye by a cationic or anionic binder such as a water soluble polymer or carrageenan. Upon exposure to normal light, the dye generates singlet oxygen that kills microorganisms and viruses. As shown in Example 4 of U.S. Pat. No. 5,820,526, no dark antimicrobial activity is observed for the compositions comprising binder, and as Comparative Example 1 shows (below), when no binder is used, the dyes leach from the substrate to such a great extent that the compositions colorize articles with which they come in contact. Japanese Patent Application No. 5-39004 discloses ionic bonding of rose bengal to a positively charged polymer carrier and killing of microbes in the presence of oxygen and light. Bezman et al. *Photochemistry and Photobiology*, 28, 325–329 (1978) disclose the photodynamic inactivation of E. coli by rose bengal immobilized on polystyrene beads. It is believed that none of these examples of polymer-bound photosensitizers such as rose bengal, however, would have antimicrobial activity in the dark.

Generally, triplet-sensitizing dye compositions intended for imparting continuous antimicrobial, self-disinfecting activity utilize the dye in combination with light, thus severely limiting applications of these compositions to those where irradiation is feasible. Thus, as an example, a floor finish comprising one of the photodynamic compositions discussed above could impart antimicrobial activity to a floor during the day, or while the flooring is otherwise irradiated with visible light, but would not impart antimicrobial activity to the flooring during dark periods. Some dyes, however, such as methylene blue and halogenated xanthene dyes such as rose bengal, possess light-independent (dark) cytotoxic activity, and thus are effective antimicrobial agents in the dark as well as in the light. See, for example, Smith et al., *Soil. Sci.*, 58, 47 (1944), Heitz et al., *Light-Activated Pesticides, ACS Symp. Ser.* 339, 1–21 (1987), and Scheffer et al., *Investigative Ophthalmology & Visual Science*, 35 3295–3307 (1994).

While the mechanism of the dark microbicidal activity of photosensitizers is unknown, it is clear that intimate contact of the photosensitizer with the microorganism is necessary. This is in contrast to the Type II mechanism of microbicidal activity of photosensitizers in the light, for which intimate contact of the photosensitizer and the microorganism is not necessary, due to the involvement of diffusible singlet oxygen. Heretofore, compositions allowing intimate contact of photosensitizer and microbe, which necessarily requires either direct application of photosensitizer in solvent (aqueous or organic), or leaching of photosensitizer from the compositions, have been avoided due to discoloration of skin and articles that come in direct physical contact with the leaching dye.

SUMMARY OF THE INVENTION

The present invention provides compositions that can be used to coat a wide variety of surfaces or form a wide variety of self-supporting polymer films or articles of a variety of shapes. The compositions include one or more polymers and one or more photosensitizers. Once a desired article (e.g., film) or coating is formed from the compositions, they are allowed to harden (e.g. cure) to form hardened polymer compositions. These hardened polymer compositions possess antimicrobial activity, preferably in the light as well as in the dark. Furthermore, they preferably do not visually colorize (i.e., discolor) skin or articles that come in contact with the resulting hardened polymer composition.

Thus, in one embodiment of the present invention, a method of limiting the presence of a microorganism is provided. The method involves contacting the microorganism with a hardened polymer composition comprising one or more polymers and one or more photosensitizers (preferably, a xanthene photosensitizer) wherein the polymer composition possesses antimicrobial activity (i.e., is capable of limiting the presence of a microorganism) in the light (e.g., room light) and the dark (i.e., the substantial absence of light). In another embodiment, an article is provided that includes a hardened polymer composition comprising one or more polymers and one or more photosensitizers wherein the polymer composition possesses antimicrobial activity in the light and the dark.

Significantly, such hardened polymer compositions and the articles that incorporate them can be produced according to the teachings of the present invention so as to not visually colorize skin or articles that contact them during use, due to the photosensitizer present in the hardened polymer composition. Conditions of use will vary depending upon the article and its application. This will be apparent to one of skill in the art.

Alternatively, such hardened polymer compositions and the articles that incorporate them can be produced according to the teachings of the present invention, which do not visually colorize, due to the photosensitizer, a piece of 95% by volume ethanol/5% by volume water solution-saturated white test paper placed in contact with the hardened polymer composition under 50-grams/cm$^2$ pressure for 5 minutes. Preferably, the $\Delta E$ value using a control portion of the test paper and a portion contacted with the hardened polymer composition is no greater than about 2.0

Preferably, at least one of the photosensitizers in the hardened polymer compositions (and the articles incorporating them) has the following formula:

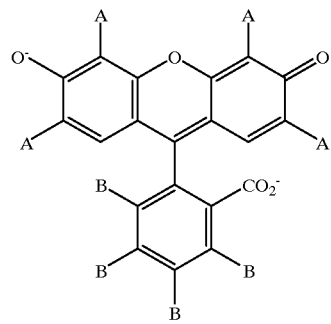

wherein the negative electric charges are balanced independently with the cations $Na^+$, $K^+$, $Li^+$, $H^+$, or substituted ammonium; each A independently represents hydrogen, chlorine, bromine, or iodine; and each B independently represents hydrogen, chlorine, bromine, or iodine. Preferred examples of such photosensitizers include those selected from the group of rose bengal, erythrosin, eosin yellowish, fluorescein, and mixtures thereof.

A hardened polymer composition of the present invention can be in the form of a coating, self-supporting film, or shaped article, for example. It can form a part of a surgical drape, a surgical face mask, pre-surgical patient prep, IV prep, handwash, dental appliance or other dental equipment, cosmetic applicator, sponge, contact lens, contact lens case, catheter (e.g., IV and urinary catheter), hospital gown, surgical glove, stethoscope, or equipment cover such as a keyboard cover or light switch cover. In addition, outdoor surfaces may also incorporate the photosensitizers of the present invention. In particular outdoor surfaces where microorganism growth can be a problem and would benefit by incorporation of the photosensitizer compositions of the present invention include roofing materials such as shingles, wooden shakes, tiles, and the like; cement and cement block; paints and stains for wood and other surfaces; road signs and the like.

Thus, the present invention provides an article comprising a hardened polymer composition comprising one or more polymers and one or more photosensitizers, at least one of which is a xanthene photosensitizer, wherein the hardened polymer composition possesses antimicrobial activity in the light and the dark and does not visually colorize white test paper saturated with a 95% by volume ethaniol/5% by volume water solution and placed in contact with the hardened polymer composition comprising the one or more photosensitizers under 50-grams/cm² pressure for 5 minutes A particularly preferred article is a contact lens case comprising a hardened polymer composition comprising one or more polymers and one or more photosensitizers wherein the hardened polymer composition possesses antimicrobial activity. Another article is a stethoscope comprising a hardened polymer composition comprising one or more polymers and one or more photosensitizers wherein the hardened polymer composition possesses antimicrobial activity. Preferably, the hardened polymer composition possesses antimicrobial activity in the light and the dark and does not visually colorize white test paper saturated with a 95% by volume ethanol/5% by volume water solution and placed in contact with the hardened polymer composition comprising the one or more photosensitizers under 50-grams/cm² pressure for 5 minutes.

The present invention also provides methods of providing an antimicrobial surface, the method comprising combining one or more polymers with one or more photosensitizers to form a surface comprising a hardened polymer composition comprising one or more polymers and one or more photosensitizers. In one embodiment the photosensitizers are preferably xanthine photosensitizers, which are used in an amount such that the hardened polymer composition possesses antimicrobial activity in the light and the dark and does not visually colorize white test paper saturated with a 95% by volume ethanol/5% by volume water solution and placed in contact with the hardened polymer composition comprising the one or more photosensitizers under 50-grams/cm² pressure for 5 minutes. Preferably the polymer is a non-cellulosic polymer and the photosensitizers are not bound to the polymer through covalent interactions. The non-cellulosic polymer is preferably a non-addition polymer.

DEFINITIONS

For the purposes of this invention, the terms "limiting the presence of a microorganism" or "antimicrobial activity" includes limiting the presence of at least one virus, at least one bacterium, at least one fungus, or a combination thereof. Limiting the presents of microrganism includes limiting the growth of a microorganism. This term also includes inhibiting, inactivating, killing, or preventing the replication of or reducing the number of a microorganism. Different terms may be used for different microorganisms.

The terms "limiting the presence of a virus," "inactivation of virus," and "viricidal activity" as used herein refer to a reduction in the amount of virus present in a sample contacted with the hardened polymer composition of this invention. Preferably, the terms refer to an at least about 50% reduction in the amount of at least one species of virus detected on a surface of the hardened polymer composition relative to the same hardened polymer without the one or to more photosensitizers under the same conditions, using the test method as described in Example 5 below. More preferably, the compositions of the present invention provide at least about 75% reduction in the amount of at least one species of virus, even more preferably, at least about 90% reduction, and most preferably, at least about 99% reduction in at least one species of virus.

The term "limiting the presence of a fungus or a bacterium" as used herein refers to methods that employ the use of hardened polymer compositions described in this invention to inhibit, kill, or prevent the replication of or reduce the number of bacteria or fungi present on a surface of the hardened polymer composition. Preferably, the term refers to an at least about 40% reduction (as evidenced by the inhibition of growth or killing, for example) in the amount of at least one species of fungus or bacterium detected on a surface of the hardened polymer composition relative to the same hardened polymer without the one or more photosensitizers under the same conditions, using the test method described in Example 6 below. For example, growth of bacteria or fungi is limited by the polymer compositions of this invention when disks cut from the hardened polymer composition preferably kill at least about 40% or more of the bacteria or fungi placed on them, in the light as well as in the dark, as evidenced by washing away the original bacteria or fungi, attempting to grow colonies on an agar surface, and observing a reduction in the number of colonies that grow in comparison to the original inoculum and a control that does not include one or more photosensitizers of the present invention. More preferably the compositions of the present invention provide at least about 75% reduction, even more preferably, at least about 90% reduction, and most preferably, at least about 99% reduction in the amount of at least one species of fungus or bacterium detected on a surface of the hardened polymer composition relative to the same hardened polymer without the one or more photosensitizers under the same conditions, using the test method described in Example 6 below.

The term "contacting" as used in the methods of this invention includes either physical contact of the polymer compositions of this invention with a virus, a bacterium, or a fungus, or exposure without direct physical contact of a virus, a bacterium, or a fungus to the hardened polymer compositions of this invention. Without intending to limit the scope of this invention, many of the photosensitizers of this invention may form diffusible substances in the light, such as singlet oxygen, which mediate an antimicrobial effect on the virus, bacterium, or fungus. Therefore, direct physical contact may not be necessary.

The term "bacteriostatic" refers herein to the property of inhibiting bacterial growth but not necessarily killing the bacteria. The term "bactericidal" refers to killing bacteria. The term "fungistatic" refers to the inhibition of replication of a fungus while the term "functicidal" refers to killing the fungus. Thus, the polymer compositions of this invention can be either bactericidal or bacteriostatic or fungicidal or fungistatic. Methods for limiting the presence of a bacterium and fungus include "cidal" (i.e., killing) activity.

The language "does not visually colorize skin or articles" as used herein means that contact of the hardened polymer composition with skin or other surface of an article does not cause the color of the skin or article to visually change color during customary use due to the photosensitizer. This does not necessarily mean that the polymer composition of the present invention is not colored itself, rather, it means that the hardened polymer composition does not transfer a significant amount of photosensitizer to skin or another article. The amount of coloration (i.e., transferred color) can be reported as a ΔE (delta E) value. "ΔE" is calculated according to the CIE 1976 Color Difference Formula, used for determining the color difference of two materials, such that $\Delta E=[(L_1-L_2)^2+(a^*_1-a^*_2)^2+(b^*_1-b^*_2)^2]^{1/2}$, wherein $L_1-L_2$ is the lightness difference between the two materials, $a^*_1-a^*_2$ is the difference in red-green light response of the two materials, and $b^*_1-b^*_2$ is the difference in blue-yellow light response of the two materials, which can be measured using various commercially-available instruments such as, for example, the Color-Difference Meter of Hunter as described by Judd and Wyszecki in Color in Business, Science, and Industry, second edition, published by John Wiley and Sons, Inc., New York, pages 295–296.

An "effective amount" of one or more of the photosensitizers of this invention refers to an amount of the photosensitizer, as a weight percentage of the dry polymer weight, that is sufficient to limit the presence of at least one of a virus, a bacterium, or a fungus.

A "hardened polymer composition" is a combination of at least one hardened polymer and at least one photosensitizer. A "hardened polymer" can be achieved by solidifying a liquid polymer, crosslinking or otherwise curing a polymer to render it insoluble, by extruding or molding a polymer, etc.

It does not necessarily mean that the polymer is hard and inflexible; rather it means that the polymer is cured or otherwise rendered solid. In fact, in certain applications such as coatings on flexible or deformable substrates a flexible "hardened" polymer composition may be preferred. Furthermore, depending on the type of polymer, a "hardened" polymer may have been cooled and solidified (as for a thermoplastic) or cured (i.e., polymerized and/or crosslinked) from polymer precursors.

BRIEF DESCRIPTIONS OF THE DRAWINGS

DETAILED DESCRIPTION OF PREFERRED EMBODIMENTS

Figure 1:
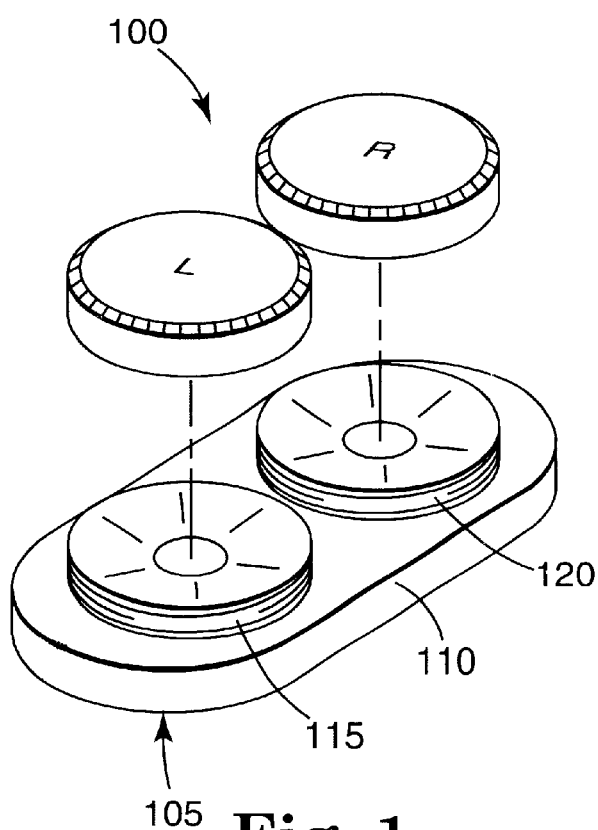
FIG. 1 is a perspective view of a contact lens case.

The present invention provides compositions that include one or more polymers and one or more photosensitizers. Preferably, the hardened polymer compositions possess antimicrobial activity in the light as well as in the dark. Furthermore, preferably, these compositions (when hardened) do not visually colorize (i.e., discolor) skin or articles that come in contact with the compositions through the transfer of the photosensitizer. Typically, the hardened polymer composition can be in the form of a coating, a self-supporting film, or other shaped article as desired.

It has been found that, while many of the polymer compositions of the present invention are very unstable toward fading prior to hardening when stored in lights the resulting hardened polymer compositions have excellent resistance toward fading when stored in light. Furthermore, a surface that includes a hardened polymer composition of the present invention will be preferably and advantageously, substantially self-disinfecting (i.e., antimicrobial), which preferably occurs in both the light and the dark. That is, it is able to kill, inactivate, or otherwise limit the presence of microorganisms in both the light and the dark. It is believed that this is possible by virtue of the generally excellent stability of the photosensitizers in a hardened polymer matrix, because of the continuous generation of singlet oxygen in the light, and because of the light-independent activity of the selected photosensitizers. Furthermore, it is believed that this light-independent activity of the photosensitizers results from a small amount of leaching of the photosensitizer from the polymer matrix. Also, it is believed that this light and dark activity are possible because the polymer and the photosensitizer are physically mixed together as opposed to covalently or ionically bound together.

Although it is believed that there is some leaching of the photosensitizer out of the polymer matrix, significantly, this is insufficient to visually colorize skin or articles with which the hardened polymer compositions come in contact during customary use. As used herein, customary use refers to the typical use of an article that includes the hardened polymer compositions of the present invention. For example, the customary and typical use of a stethoscope that includes a polymer membrane coated with, or made out of a polymer composition of the present invention includes placing the membrane against skin or clothing and wiping it with an alcohol-saturated cloth at room temperature. Under such conditions, the skin, clothing, and cloth are not discolored by the photosensitizer.

Preferably, the value of $\Delta E$ of the skin or article with which the hardened polymer compositions of the present invention come in contact is no greater than about 2.0, due to the photosensitizer. A difference in color of two materials having a $\Delta E$ value of no greater than about 2.0 is generally regarded as being indiscernible to the human eye. The degree of coloration can be determined upon contacting a hardened polymer composition of the present invention containing a photosensitizer of the present invention with a piece of 95% by volume ethanol/5% by volume water solution-saturated white paper Hammermill Laserprint paper, item #00460-4, a product of International Paper, Memphis, Tenn.) under 50-grams/cm$^2$ pressure for 5 minutes and then measuring the La*b* values. In this test, the La*b* values are measured for a control area of the paper as well as for the portion of paper that is contacted with the polymer composition, using D65 illuminant and a Colortron II Colorimeter (LightSource, San Rafael, Calif.), and the $\Delta E$ values are calculated from the L*a*b* data. A $\Delta E$ value of no greater than about 2.0 denotes a polymer composition that does not colorize articles that come into contact with it due to the photosenisitizer.

Significantly, both DNA and RNA viruses (including RNA retroviruses) are inactivated, and Gram-negative bacteria, Gram-positive bacteria, and fungi are limited in growth, using the polymer compositions of the present invention.

There are a variety of viruses that can be inactivated using the methods of this invention. These viruses include viruses with single or double-stranded nucleic acid genomes, DNA or RNA viruses and including enveloped as well as some non-enveloped viruses. Preferred viruses that are inactivated using the polymer compositions of the present invention are enveloped viruses. The examples (below) provide specific exemplary methods for determining whether a particular species of virus, fungus, or bacterium is inhibited by the polymer compositions of this invention. Those of ordinary skill in the art of microbiology will be able to determine whether a particular compound of this invention limits the presence of a virus, a bacterium, or a fungus according to this invention, and in view of the art of microbiology, without undue experimentation.

Viruses that comprise negative single-stranded RNA genomes include Orthomyxoviridae, Rhabdoviridae, Paramyxoviridae, Bunyaviridae, and Filoviridae. These are enveloped viruses. Orthomyxoviridae include the influenza viruses A, B, and C. Rhabdoviridae include rabies virus and vesicular stomatitis virus. Paramyxoviridae include parainfluenza virus of mammals (including mumps virus) and pneumovirus (such as respiratory syncytial viruses of man and cattle). Bunyaviridae include hantavirus, which causes Korean hemorrhagic fever and hantavirus pulmonary syndrome. Filoviridae include Marburg virus and Ebola virus.

Viruses that comprise positive single-stranded RNA genomes include Picornaviridae (non-enveloped), Retroviridae, and Togaviridae, Picornaviridae include polioviruses, coxsackieviruses, hepatitis A virus, and rhinovirus. Retroviridae include, for example, human immunodeficiency virus (HIV), simian immunodeficiency virus (SIV), and equine infectious anemia virus (EIAV). Togaviridae include Semliki Forest virus, yellow fever virus, Dengue virus, tick-borne virus, and rubella virus. Parvovirus (non-enveloped) is the only virus having a single-stranded negative-sense DNA genome. This virus primarily infects cats and dogs.

All other DNA viruses are double-stranded. Double stranded viruses include Papovaviridae, Adenoviridae, Herpesviridae, Poxviridae, and Hepadnaviridae. With the exception Herpesviridae, these viruses are non-enveloped viruses. Papovaviridae include papillomaviruses causing warts and tumors. Adenoviridae include Mastadenovirus and a variety of viruses capable of infecting the respiratory tract. Herpesviridae include herpes simplex 1 and 2, varicella zoster virus, cytomegalovirus, Epstein-Barr virus, human herpesvirus 6, antibodies to which are now known to be responsible for multiple sclerosis, and human herpesvirus 7. Poxviridae include variola and other pox-producing viruses. Hepadnaviridae include human hepatitis B virus.

A variety of bacteria are growth inhibited by the polymer compositions of this invention. These include, but are not limited to *Entertococcus faecium, Staphylococcus aureus, Pseudomonas aeruiginosa*, and *Escherichia coli*. Other bacteria that can be tested for growth inhibition in the presence of the polymer compositions of this invention, include, but are not limited to, other species of Staphylococcus, Entertococcus, Streptococcuts, Corynebacterium, Listeria, Neisseria, and Enterobacteriaceae (which includes the genera Escherichia, Salmonella, and Shigella). The coliforms are Gram-negative rods, generally in the family Enterobacteriaceae. Some coliforms colonize the intestinal tract of humans and other animals. Some coliforms are associated with disease. Surfaces and liquids contaminated with these bacteria can be exposed to the polymer compositions of this invention to limit their pathogenic potential. Several pathogenic species of fungi exist, including *Candida albicans*, which causes yeast infection of the oral cavity known as thrush and an infection of the female reproductive tract known as vulvovaginitis. *Candida albicans* is becoming increasingly common as an agent causing infection and pathogenic sequelae. Those of ordinary skill in the art of microbiology will appreciate that various fungi can be tested for their sensitivity to the compounds of this invention.

In the context of photodynamic killing (and inactivation) of microorganisms, a photosensitizer is a chemical that absorbs light and causes the formation of reactive oxygen species, such as singlet oxygen. Suitable photosensitizers for the present invention are those that display both light and dark microbicidal activity. As used herein, "light activity" refers to limiting the presence of microorganisms when the photosensitizer is exposed to light, such as that from a directed light source or from ambient light. As used herein, "dark to activity" refers to limiting the presence of microorganisms when the photosensitizer is in the dark (i.e., when there is substantially no visible light present).

Suitable photosensitizers can be covalently bound to a polymer of the composition, although preferably the photosensitizers are not covalently bound. Examples of classes of such photosensitizers include the xanthene dyes. the triphenylmethine dyes, and the oxazine dyes. Although the scope of the polymer compositions of the present invention is not so limited, preferably, the photosensitizer is a xanthene dye of the following formula:

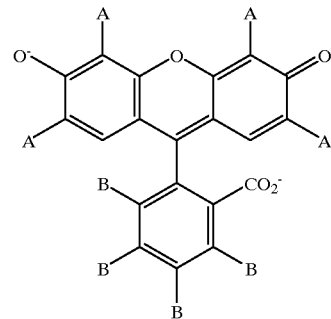

wherein the negative electric charges are balanced independently with the cations $Na^+$, $K^+$, $Li^+$, $H^+$ or substituted ammonium; each A independently represents hydrogen, chlorine. bromine, or iodine; and each B independently represents hydrogen, chlorine, bromine, or iodine.

The xanthene photosenisitizers of the present invention can be purchased from a chemical supplier or prepared according to methods known to those skilled in the art of organic synthesis. Examples of xanthene photosensitizers that can be purchased include rose bengal, where A=I and B=Cl in the formula above; erythrosin, where A=I and B=H; phloxin B, where A=Br and B=Cl; eosin yellowish, where A=Br and B=H; and fluorescein, where A=H and B=H.

The polymers of the present invention can be purchased from a chemical supplier or prepared according to methods known to those skilled in the art of polymer synthesis. A variety of polymers can be used in the invention. The polymer is preferably chosen to resist attack by singlet oxygen. They can be thermoplastic resins or thermoset resins (e.g., curable resins). They can be capable of covalently bonding to the photosensitizer or not, depending on the desired result. The invention is not necessarily limited by the class of polymer.

Examples of suitable polymers include, but are not limited to, addition polymers, for example, acrylate (such as that disclosed in U.S. Pat. No. 5,585,407 (Patel), acrylic, vinyl, and olefinic polymers; polyacrylates, polyurethanes; regenerated cellulose, for example, viscose rayon; cellulose esters, for example, cellulose acetate; condensation polymers such as polyesters; polycarbonates; polyethers; polyimides, polyureas, and polyamines, as well as copolymers. Certain silicone elastomers such as those formed by hydrosilation and silane condesation reactions as well as epoxy resins may also be suitable. Suitable polymers may be obtained in a water- or solvent-soluble solid form or as a dispersion or emulsion in water or solvent. Examples of commercially available polymers include STANCE floor finish (3M Company, St. Paul, Minn.), VITEL polyester (Goodyear Chemicals, Akron, Ohio), and polycarbonate resin (Aldrich Chemical, Milwaukee, Wis.). Preferably, for certain embodiments, the polymer is coatable, but this is not a necessary requirement. For other embodiments, the polymer is extrudable. In certain particularly preferred embodiments, non-cellulosic polymers are preferred, and non-addition polymers are even more preferred, due to the carbon-carbon double bonds with allylic hydrogens that are present in many olefinic addition polymers and the polymer degradation that can result as a result of reaction with singlet oxygen. The concentration of the photosensitizer as a percentage of the dry polymer weight, the light source, intensity or irradiance, spectral properties of the light source, and duration of the illumination can affect the performance of the polymer compositions. Those of ordinary skill in the art will appreciate that concentration, light intensity, and the like can be optimized in view of this specification without undue experimentation. Methods are provided in the examples for preferred techniques and formats for optimizing the growth-inhibiting properties of these polymer compositions. Other testing regimes can be readily generated by those skilled in the art, particularly in view of the guidance provided throughout the examples and in view of clinical laboratory testing standards and manuals. Preferred concentration of the photosensitizer as a percentage of the dry polymer weight (reported as a weight percent or wt-%) will vary depending on use. A preferred concentration is from about 0.01 wt-% to about 10 wt-%, based on the total weight of the composition upon addition of the photosensitizer; however, many of the compositions will be active at lower concentrations of photosensitizer as a percentage of the dry weight of the polymer. The concentration for some of the hardened polymeric compositions will be reduced upon rinsing, as described herein.

In certain embodiments, the antimicrobial polymer composition can be dissolved in a suitable solvent, such as an organic solvent, or water, and may be applied to a surface by a number of methods. Alternatively, the composition may be in the form of a dispersion in water or solvent, or may be coated as 100% solids as a hot melt or reactive system. Such methods include, for example, wiping the composition onto a surface with a cloth or sponge, pouring the composition onto a surface and spreading it with a mop, squeegee, sponge, or cloth, dispensing the composition propelled as an aerosol from a suitable pressurized container, and providing the composition in sufficient concentrations on a cloth or other absorbent carrier and packaging the premoistened carriers for disposable use. The liquid composition is preferably coated at a thickness to form a residual film of about 0.01 millimeter (mm) to about 5 mm.

Hardened antimicrobial polymer compositions can also be prepared by applying a photosensitizer to a prehardened polymer. For example, U.S. Pat. No. 5,340,614 discloses impregnation of polymers with photosensitizers such as rose bengal using supercritical carbon dioxide. Such an application method results in a physical mixture of the polymer and the photosensitizer.

Free-standing films and articles comprising the polymer compositions of the present invention can be prepared by a variety of techniques, including extrusion and injection molding. Such techniques are well known to one of skill in the art. Typically, once the polymer is hardened (e.g., dried or cured, for example), the polymer composition is washed with water, preferably a constantly refreshed stream of water (which can be tap water if desired), at a temperature of at least about 50° C., and typically no more than about 80° C., for a period of time sufficient to remove excess dye that may transfer stain. For example, in the laboratory the rinsing step may take as little as 2 hours and typically no more than about 24 hours to complete. If the original hardened polymer does not colorize white paper saturated with 95:5 ethanol:water by volume, as described above, then the polymer composition does not need to be washed.

Light exposure, if light is present, can include exposure from a directed light source or from ambient light. Preferably, if light exposure is desired, the polymer compositions of this invention are exposed to light of a wavelength of at least about 200 nanometers (nm) and less than about 900 nm.

More preferably, the light has a wavelength of at least about 400 nm and less than about 850 nm. Convenient and sufficient light sources are those typically used for fluorescent lighting of laboratories and offices as well as Light Emitting Diode (LED) sources, incandescent sources, sunlight, and lasers. Reflected light from any of these sources may also be suitable. The individual polymer compositions of this invention can optimally be activated with a particular wavelength of light. Without intending to limit the scope of this invention, the spectral output of the light source likely overlaps with the absorption spectrum of the photosensitizer of the polymer composition as measured in the polymer composition. In one embodiment, the polymer compositions are exposed to an irradiance of at least 270 $\mu W/cm^2$ for about five minutes, but those of ordinary skill in the art will readily appreciate that brighter light sources allow for reductions in the duration of illumination time.

Light exposure, if desired, can occur with continuous, pulsating, or periodic exposure to light. Those with ordinary skill in the art will recognize that optimal activation will depend on the intensity and the duration of light, but that a range of intensities and durations of light exposure can be used to activate the light-responsive polymer compositions of this invention.

The antimicrobial polymer compositions of the present invention can be used to make coatings, self-supporting (i.e., free-standing) films, and other shaped articles in a wide variety of articles, particularly medical devices, to combat diseases that can be spread by a wide variety of microorganisms. For example, coatings of the antimicrobial polymer compositions can be used on hard surfaces found in homes, hospitals, schools, and the work place, such as glazed and unglazed tile, brick, porcelain, ceramics, metals, glass, wood, and hard plastics such as polystyrenes, vinyls, acrylics, polyesters, and the like.

Whether in the form of coatings, films, or articles of other shapes, examples of such articles include surgical drapes, dental appliances, dental equipment, cosmetic applicators, sponges, contact lenses, contact lens cases, intravenous catheters, urinary tract catheters, hospital gowns, surgical gloves, stethoscopes, computer keyboard covers, counter tops, cutting boards, toilet seats, telephones, floors, bed rails, walls, doors, door knobs, light switches and covers, sink handles, and the like. Outdoor surfaces where microorganism growth can be a problem and would benefit by incorporation of the photosensitizer compositions of the present invention include roofing materials such as shingles, wooden shakes, tiles, and the like; cement and cement block; paints and stains for wood and other surfaces; road signs and the like. Non-photosensitizing antimicrobial agents may also be added to these compositions, including antibiotics, trichlosan, etc.

A particularly preferred article is a contact lens case that includes a hardened polymer composition with one or more polymers and one or more photosensitizers therein. The hardened polymer composition possesses antimicrobial activity as described herein. The case itself, or a portion thereof, can be formed from the polymer composition. Alternatively, the case can include therein a pellet, for example, formed from the polymer composition. An example of a contact lens case is shown in FIG. 1, and is described in more detail in U.S. Pat. No. 5,452,792 (Zautke et al.) Briefly, referring to FIG. 1, a contact lens case 100 is typically made of a molded plastic material. The contact lens case 100 includes a base 105 having a flat, oblong portion 110 and a molded pair of threaded containers 115 and 120. The containers 115 and 120 are threaded and generally cylindrical in shape with an interior construction having a smooth, bowl-like orientation to prevent the contact lenses usually stored in a liquid disinfectant from being scratched when placed within or extracted from the containers 115 and 120.

Figure 2:
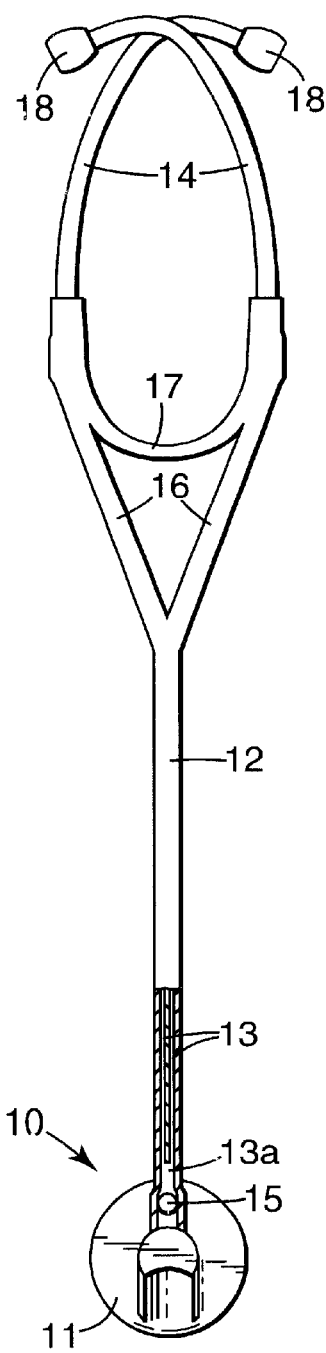
FIG. 2 is an elevational view of a stethoscope.

Another article is a stethoscope that includes a hardened polymer composition with one or more polymers and one or more photosensitizers. The hardened polymer composition possesses antimicrobial activity as described herein. The stethoscope includes a polymer membrane, For example, that can be coated with the polymer composition of the present invention. Alternatively, the polymer membrane itself, and/or other parts of the stethoscope (e.g., tubing, ear tips) can be formed from the polymer composition. An example of a stethoscope is shown in FIG. 2, and is described in more detail in U.S. Pat. No. 4,440,258 (Packard). Briefly, referring to FIG. 2, stethoscope head 10 comprises body member 11, which can be in the form of a polymeric membrane.

Stethoscope head 10 is attached to a headset that includes elongated flexible tubing 12 which contains dual air passages 13 which run side-by-side for a major portion of the distance between stethoscope head 10 and ear tubes 14. In the lower end of flexible tubing 12 which attaches to stethoscope head 10, passages 13 merge into a single passage 13a adapted to be coupled to stern fitting 15 of stethoscope head 10. The upper end of flexible tubing 12 bifurcates into coupling arms 16, each of which attaches to one of the ear tubes 14 and each of which contains one of the ear tips 18. Ear tubes 14 are secured together by tubing 17 which encloses a spring (not shown).

EXAMPLES

Objects and advantages of this invention are further illustrated by the following examples, but the particular materials and amounts thereof recited in these examples, as well as other conditions and details, should not be construed to unduly limit this invention.

I. Preparation of the Polymer Compositions

Reagents for preparation of the polymer compositions were obtained from Aldrich (Milwaukee, Wis.) unless otherwise noted.

Example 1

Preparation of a Polymer Composition Comprising a Polycarbonate and a Dye

Polycarbonate resin (10 grams (g), Aldrich Cat. No. 18,162-5) was dissolved in enough dichloromethane to make a solution with total volume of 100 milliliters (ml) by mixing overnight (approximately 16 hours) at room temperature (approximately 25° C.) using a ball roller. To 10 g of this solution was added a dye, such as the disodium salt of rose bengal (10 milligrams (mg) for 1% solution; 5 mg for 0.5% solution; 2.5 mg for 0.25% solution), for example, after which mixing was continued for an additional 8 hours. The polymer composition was then applied to various surfaces and articles by dipping of the surface or article in the polymer composition and then drying first at 60° C. for 1 hour, washing the coated surface or article with a 50° C. stream of water for 2 hours, and then drying in a forced-air oven at 100° C. for 12 hours. The coated surfaces and articles were then tested for microbicidal activity as described below.

Example 2

Preparation of a Polymer Composition Comprising a Polyester and a Dye

VITEL polyester resin (10 g, Goodyear Chemicals, Akron, Ohio) was dissolved in enough dichloromethane to make a solution with a total volume of 100 ml by mixing overnight at room temperature using a ball roller. To 10 g of this solution was added a dye, such as the disodium salt of rose bengal (10 mg for 1% solution; 5 mg for 0.5% solution; 2.5 mg for 0.25% solution), for sample, after which mixing was continued for an additional 8 hours. The polymer composition was then applied to various surfaces and articles by dipping of the surface or article and then drying first at 60° C. for 1 hour, washing the coated surface or article with a 50° C. stream of water for 2 hours, and then drying in a forced-air oven at 100° C. for 12 hours. The coated surfaces and articles were then tested for microbicidal activity as described below.

Example 3

Preparation of a Polymer Composition Comprising a Polyacrylate and a Dye

To STANCE Floor Finish (50 g, 3M Company, St. Paul, Minn.), comprising a styrene-acrylate copolymer emulsion having 18% solids in water. was added solid dye, such as rose bengal, disodium salt (1.8 mg for 0.02% solution of dye based on polymer solids; 0.9 mg for 0.01% solution of dye based on polymer solids), for example, and the solution was applied to a floor tile by dipping and then drying, without washing, at 25° C. for 30 minutes.

II. Microbicidal Testing

Reagents for microbicidal testing of the polymer compositions were obtained from Aldrich (Milwaukee, Wis.) unless otherwise noted.

Example 4

Testing of Microbicidal Activity of Rose Bengal, Toluidine Bule O, Crystal Violet, and Methylene Blue Against Bacteria and Fungi Rose bengal, toluidine bule O, crystal violet, and methylene blue each was dissolved in water to give several milliliters of a solution that had a final concentration of 10 mg/ml. The procedure used for testing for antibacterial and antifungal activity is as follows.

Bacteria or fungi stock was plated onto Trypticase Soy Broth (TSB) agar (Becton Dickinson, Cockeysville, Md.) and incubated at 37° C. overnight, at which time several colonies were transferred to phosphate buffered saline (PBS) to give a solution with final concentration of $10^6$ bacteria/ml or fungi/ml, as determined by comparison of turbidity with McFarland standards. Subsequently, a lawn of the bacterium or fungus was prepared by triple swabbing a Trypticase Soy broth agar plate (prepared using TSB and agar according to label instructions). Then, 6-mm diameter paper filter disks were dipped into one of the dyed solutions, blotted to remove the excess solution, and placed on the agar plates. Each plate was then either kept in the dark (control) or irradiated for 15 minutes in room light or for overnight in room light before incubation at 37° C. for 24 hours.

The plates were removed from the incubator and inspected for clear areas surrounding treated 6-mm filter disks that are indicative of prevention of growth of bacteria. The diameter of each clear area was measured and recorded and compared with controls. The results for this experiment are reported below in Table 1.

The results in Table 1 indicate that all four photosensitizers have antimicrobial activity in the dark, as well as in the light, against some organisms tested.

TABLE 1

| Photosensitizer | Organism | Zone of Inhibition in Dark | Zone of Inhibition in Room Light, 15 Minutes | Zone of Inhibition in Room Light Overnight |
| --- | --- | --- | --- | --- |
| Methylene Blue | Staph. Aureus | 18 mm | 20 mm | 28 mm |
| Methylene Blue | E. faecium | 16 mm | 16 mm | 19 mm |
| Methylene Blue | C. albicans | 12 mm | 12 mm | 18 mm |
| Methylene Blue | P. aeruginosa | 0 mm | 0 mm | 0 mm |
| Methylene Blue | Salmonella spp. | 0 mm | 0 mm | 0 mm |
| Methylene Blue | E. coli | 8 mm | 0 mm | 0 mm |
| Rose Bengal disodium salt | Staph. Aureus | 23 mm | 21 mm | 36 mm |
| Rose Bengal disodium salt | E. faecium | 19 mm | 19 mm | 34 mm |
| Rose Bengal disodium salt | C. albicans | 0 mm | 0 mm | 13 mm |
| Rose Bengal disodium salt | P. aeruginosa | 0 mm | 0 mm | 13 mm |
| Rose Bengal disodium salt | Salmonella spp. | 7 mm | 8 mm | 19 mm |
| Rose Bengal disodium salt | E. coli | 0 mm | 0 mm | 11 mm |
| Crystal Violet | Staph. Aureus | 30 mm | 30 mm (after 30 min.) | |
| Toluidine Blue O | Staph. Aureus | 20 mm | 19 mm (after 30 min.) | |

Example 5

Testing of Polymer Compositions for Viricidal Activity Against Human Immunodeficiency Virus 1 (HIV-1)

This test may be performed by Southern Research Institute, Frederick, Md., according to the following procedure. RF virus and MT2 cells are obtained from NIAII) AIDS Research and Reference Reagent Program.

Concentrated HIV/RF strain (0.1 ml) is placed onto a 6 mm disk of the polymer composition situated in a well of a 24-well plate. The plate is allowed to sit in the dark or under regular fluorescent lighting on the lab benchtop for 30 minutes. An untreated control is run for each concentration tested. Next, serial dilutions are made from the well samples and used to inoculate MT2 cells at $10^4$ cells/well. Plates are incubated at 37° C., 5% $CO_2$ for seven days. The results are reported as Log Reduction in Virus Titer.

Example 6

Testing of Polycarbonate Compositions for Antibacterial Activity Against Staphylococcus Aureus and Measurement of ΔE LITTMANN stethoscope diaphragms (un-printed, no holes at perimeter, 3M Company, St. Paul, Minn.) were treated with polycarbonate resin as described above in Example 1. Measurement of ΔE was done by contacting the stethoscope diaphragm with a piece of 95% by volume ethanol/5% by volume water solution-saturated white test paper (Hammermill Laserprint paper, item #00460-4, a product of International Paper, Memphis, Tenn.) under 50 g/cm² pressure for 5 minutes and then measuring the L*b* values. The, La*b* values were measured for a control area of each paper as well as for the portion of paper that was contacted with the polymer composition, using D65 illuminant and a Colortron II Colorimeter (LightSource, San Rafael, Calif.), and the ΔE values were calculated from the L*a*b* data. A ΔE value of no greater than about 2.0 denotes a polymer composition that does not colorize articles that come in contact with it.

Staphylococcus aureus (ATCC # 12601) stock was plated onto TSB agar and grown up at 37° C. overnight (approximately 16 hours), at which time several colonies were transferred to PBS to give a solution with final concentration of $10^4$ bacteria/ml. Twenty microliters of that solution were diluted with 10 ml PBS buffer, vortexed, and plated in a deep agar plate as positive control, labeled "inoculum" in the table below.

Alternatively, 20 microliters of the $10^4$ bacteria/ml solution were placed on a dyed diaphragm (indicated below as % dye based on solids of polyester solution) and irradiated for 30 minutes using room light, by placing on the lab bench, and then diluted with 10 ml PBS buffer, vortexed, and plated in a deep agar plate.

Alternatively, 20 microliters of the $10^4$ bacteria/ml solution were placed on one of the dyed diaphragms (indicated below as % dye based on solids of polyester solution) and placed in the dark for 30 minutes, and then diluted with 10 ml PBS buffer, vortexed, and plated in a deep agar plate.

All deep agar plates were incubated for 24 hours at 37° C., after which colonies were counted and recorded below.

All microbiology tests were done in triplicate. The numbers in Table 2 are average values computed from the three runs.

as well as in the light and do not colorize a surface as evidenced by ΔE values no greater than about 2.0.

It will be readily understood by those skilled in the art that the test methods outlined above will allow one, without undue experimentation, to determine whether a particular formulation of photosensitizer in a particular polymer will be useful in limiting growth of microorganisms, without colorizing surfaces.

Example 7

Testing of a Polyester Composition for Antibacterial Activity Against *Staphylococcus Aureus*

LITTMANN stethoscope diaphragms were treated with VITEL polyester resin as described above in Example 2 and

TABLE 2

| Sample Identification | Staph. Aureus inoculum | Number of colonies [dark] | Percent Reduction [dark] | Number of colonies [room light] | Percent Reduction [room light] | delta E |
|---|---|---|---|---|---|---|
| 1% rose bengal disodium salt in polycarbonate | approx. 300 | 1 | 99 | 0 | 100 | 0.00 |
| Control - polycarbonate only | approx. 300 | 207 | 31 | 184 | 5 | |
| 1% crystal violet in polycarbonate | approx. 300 | 201 | 33 | 192 | 69 | 0.251 |
| 1% toluidine blue in polycarbonate | approx. 300 | 180 | 40 | 184 | 39 | 0.184 |
| 0.25% rose bengal disodium salt in polycarbonate | approx. 300 | 7 | 64 | 1 | 99 | 0.266 |
| 0.25% rose bengal triethyl ammonium salt in polycarbonate | | | | | | 0.391 |
| 0.25% rose bengal disodium salt in polycarbonate (dried 1 hour only at 60° C.) | | | | | | 0.346 |
| 0.25% rose bengal triethyl ammonium salt in polycarbonate (dried 1 hour at 60° C. only) | | | | | | 3.194 |

The results in Table 2 indicate that crystal violet and toluidine blue polycarbonate compositions, in contrast to their aqueous solutions, do not limit the growth of bacteria according to the definition stated above. Additionally, 0.25% rose bengal triethylammonium salt, in polycarbonate, dried only 1 hour at 60° C., colorized the ethanol-saturated paper surface it contacted as evidenced by the ΔE value of 3.194.

On the other hand, the polymer compositions prepared using the disodium salt of rose bengal, at 0.25% as well as at 1% concentrations, limit the growth of bacteria in the dark tested for their ability to limit the growth of Staphylococcus aureas. All microbiology tests were done in triplicate. The numbers in Table 3 are average values computed from the three runs.

The results in Table 3 indicate that rose bengal polyester compositions limit the growth of bacteria in the dark as well as in the light according to the present invention.

TABLE 3

| Sample Identification | Staph. aureus inoculum | Number of colonies [dark] | Percent Reduction [dark] | Number of colonies [room light] | Percent Reduction [room light] | delta E |
|---|---|---|---|---|---|---|
| 1% rose bengal disodium salt in VITEL | 177 | 0 | 100 | 0 | 100 | 1.718 |
| Control-VITEL only | 177 | 139 | 21 | 125 | 29 | |

Example 8

Testing of a Polyacrylate Composition for Antibacterial Activity Against *Staphylococcus Aureus*

Floor tiles were treated with STANCE floor finish as described above and tested for their ability to limit the growth of *Staphylococcus aureus*. All microbiology tests were done in triplicate. The numbers in Table 4 are average values computed from the three runs.

The results in Table 4 indicate that rose bengal polyacrylate compositions limit the growth of bacteria in the dark as well as the light according to the present invention. In contrast, toluidine blue and crystal violet polyacrylate compositions do not limit the growth of bacteria in the light or in the dark, even though their aqueous solutions limited growth of bacteria in the light and in the dark.

concentration of $10^4$ bacteria/mil. Twenty microliters of that solution were diluted with 10 ml PBS buffer, vortexed, and plated in a deep agar plate as positive control, labeled "inoculum" in the table below.

Alternatively, 20 microliters of the $10^4$ bacteria/ml solution were placed on a dyed diaphragm (indicated below as % dye based on solids of polyester solution) and irradiated for 10 minutes using room light, by placing on the lab bench, and then diluted with 10 ml PBS buffer, vortexed, and plated in a deep agar plate.

Alternatively, 20 microliters of the $10^4$ bacteria/ml solution were placed on one of the dyed diaphragms (indicated below as % dye based on solids of polyester solution) and placed in the dark for 10 minutes, and then diluted with 10 ml PBS buffer, vortexed, and plated in a deep agar plate.

TABLE 4

| Sample Identification | *Staph. aureus* inoculum | Number of colonies [dark] | Percent Reduction [dark] | Number of colonies [room light] | Percent Reduction [room light] | Delta E |
|---|---|---|---|---|---|---|
| 0.02% toluidine blue in STANCE | approx. 300 | 255 | 15 | 241 | 20 | 0.149 |
| Control-STANCE only | 221 | 190 | 14 | 197 | 11 | |
| 0.02% crystal violet in STANCE | approx. 300 | 250 | 17 | 268 | 11 | 0.547 |
| 0.02% rose bengal disodium salt in STANCE | 161 | 44 | 73 | 2 | 94 | 0.441 |

Example 9

Testing of Rose Bengal and Phloxin B Polycarbonate Compositions for Antibacterial Activity Against *Staphylococcus Aureus*

LITTMANN stethoscope diaphragms were treated with phloxin TBS in polycarbonate resin as described above in Example 1.

*Staphylococcus aureus* (ATCC #12601) stock was plated onto TSB agar and grown up at 37° C. overnight (approximately 16 hours), at which time several colonies were transferred to PBS (buffer) to give a solution with final All deep agar plates were incubated for 24 hours at 37° C. after which colonies were counted and recorded below.

All tests were done in triplicate. The numbers in Table 5 are average values computed from the three runs.

The results in Table 5 indicate that rose bengal- and phloxin B-containing polycarbonate compositions limit the growth of bacteria in the dark as well as in the light according to the present invention, after only 10 minutes contact time with the bacteria.

TABLE 5

| Sample Identification | *Staph. Aureus* inoculum | Number of colonies [dark, 10 minutes] | Percent Reduction [dark, 10 minutes] | Number of colonies [room light, 10 minutes] | Percent Reduction [room light, 10 minutes] |
|---|---|---|---|---|---|
| 10.0% rose bengal disodium salt in polycarbonate | 147 | 6 | 96 | 0 | 100 |
| Control - polycarbonate only | 147 | 190 | 0 | 197 | 0 |
| 1.0% rose bengal disodium salt in polycarbonate | 147 | 36 | 76 | 26 | 82 |
| 0.25% rose bengal disodium salt in polycarbonate | 168 | 16 | 90 | 4 | 98 |
| 0.25% phloxin B disodium salt | 168 | 90 | 46 | 2 | 99 |

Example 10

Testing of Rose Bengal Polycarbonate Compositions for Antibacterial Activity Against *Staphylococcus Aureus*

LITTMANN stethoscope diaphragms were treated with polycarbonate resin as described above in Example 1.

*Staphylococcus aureus* (ATCC #12601) stock was plated onto TSB agar and grown up at 37° C. overnight, at which time several colonies were transferred to PBS (buffer) to give a solution with final concentration of $10^4$ bacteria/ml. Twenty microliters of that solution were diluted with 10 ml PBS buffer vortexed, and plated in a deep agar plate as positive control, labeled "inoculum" in the table below.

Alternatively, 20 microliters of the $10^4$ bacteria/ml solution were placed on a dyed diaphragm (indicated below as % dye based on solids of polyester solution) and irradiated for 30 minutes using room light, by placing on the lab bench, and then diluted with 10 ml PBS buffer, vortexed, and plated in a deep agar plate.

Alternatively, 20 microliters of the $10^4$ bacteria/ml solution were placed on one of the dyed diaphragms (indicated below as % dye based on solids of polyester solution) and placed in the dark for 30 minutes, and then diluted with 10 ml PBS buffer, vortexed, and plated in a deep agar plate.

All deep agar plates were incubated for 24 hours at 37° C. after which colonies were counted and recorded below.

After following this procedure nine times, using the same disks, the procedure was run an additional time. The numbers presented in Table 6 below are for the tenth challenge of stethoscope disks. All tests were done in triplicate.

The results in Table 6 indicate that rose bengal polycarbonate compositions limit the growth of bacteria in the dark as well as in the light according to the present invention, even after multiple challenges.

TABLE 6

| Sample Identification | Staph. Aureus inoculum | Number of colonies [dark, 10 minutes] | Percent Reduction [dark, 10 minutes] | Number of colonies [room light, 10 minutes] | Percent Reduction [room light, 10 minutes] |
|---|---|---|---|---|---|
| 0.5% rose bengal disodium salt in polycarbonate | 183 | 0 | 100 | 0 | 100 |
| Control - VITEL only | 183 | 132 | 28 | 138 | 25 |
| Control - polycarbonate only | 183 | 152 | 17 | 120 | 34 |
| 1.0% rose bengal disodium salt in polycarbonate | 183 | 0 | 100 | 0 | 100 |
| 1.0% rose bengal disodium salt in VITEL | 183 | 15 | 92 | 0 | 100 |

Example 11

Testing of Rose Bengal-Comprising Polycarbonate Compositions for Antibacterial Activity Against *Enterococcus faecium*

LITTMANN stethoscope diaphragms were treated with polycarbonate resin as described above in Example 1 and tested for their ability to limit the growth of *Enterococcus faecium* (ATCC #49332) according to the procedure described in Example 10 (except that the stethoscope diaphragm disks had not been previously challenged and the challenge organism was *E. faecium*).

All tests were done in triplicate. The numbers in the Table 7 are average values computed from the three runs.

The results in Table 7 indicate that the rose bengal-containing polycarbonate composition limits the growth of *E. faecium*.

TABLE 7

| Sample Identification | E. faecium inoculum | Number of colonies [dark, 30 minutes] | Percent Reduction [dark, 30 minutes] | Number of colonies [room light, 30 minutes] | Percent Reduction [room light, 30 minutes] |
|---|---|---|---|---|---|
| 1.0% rose bengal disodium salt in polycarbonate | 8272 | 6 | 99 | 61 | 99 |
| Control - polycarbonate only | 8272 | 6995 | 15 | 6710 | 19 |

Example 12

Testing of Rose Bengal-Containing Polycarbonate and Polyester Compositions for Antibacterial Activity Against *Pseudomonas Aeruginosa*

LITTMANN stethoscope diaphragms were treated with polycarbonate resin or polyester resin as described above in Example 1 and tested for their ability to limit the growth of *Pseudomonas aeruginosa* (ATCC #9027) according to the procedure described in Example 11 (except that contact time of bacteria and stethoscope diaphragms was 60 minutes and challenge organism was P. aeruginosa).

All tests were done in triplicate. The numbers in Table 8 are average values computed from the three runs. Note: Bright light indicates samples were irradiated 6 inches distant from two Phillips 15 W daylight bulbs (irradiance= 1.35 mW/cm$^2$.

The results in Table 8 indicate that rose bengal-containing polymer compositions limit the growth of Pseudomonas aeruginosa in the dark as well as in the light. The results also indicate that the control samples limited the growth of this organism in room light as well as bright light.

TABLE 8

| Sample Identification | P. aeruginosa inoculum | Number of colonies [dark, 60 min.] (Percent Reduction) | Number of colonies [room light, 60 min.] (Percent Reduction) | Number of colonies [bright light, 60 min.] (Percent Reduction) |
| --- | --- | --- | --- | --- |
| 1.0% rose bengal disodium salt in polycarbonate | 167 | 64 (62) | 62 (63) | 31 (81) |
| 1.0% rose bengal disodium salt in VITEL | 167 | 40 (76) | 44 (74) | 10 (94) |
| Control - polycarbonate only | 167 | 108 (35) | 59 (65) | 44 (74) |
| Control - VITEL only | 167 | 110 (34) | 72 (57) | 45 (73) |

Example 13

Testing of Rose Bengal-Containing Polycarbonate Composition for Antibacterial Activity Against Serratia Marcescens Translucent plastic pill boxes (manufactured by Flents Co., used as models for contact lens cases) were treated (except for the control) with polycarbonate resin comprising 1% rose bengal as described in Example 1 and tested for their ability to limit the growth of Serratia marcescens (ATCC #14041) by contacting them with 5 ml bacteria-laden PBS buffer (5.6×10$^5$ cfu/ml) and irradiating with the same light source as in Example 12, for four hours. (No dark runs were conducted.) The sample buffer solutions were then placed into deep agar plates and then incubated for 48 hours, after which colonies were counted. The numbers in Table 9 are average values of log reduction of viable colonies computed for the three runs.

The results indicate that large numbers of bacteria can be killed using the methods of the present invention.

TABLE 9

| Sample Identification | Log reduction of viable colonies [bright light, 4 hours] |
| --- | --- |
| Contact lens case treated with 1.0% rose bengal disodium salt in polycarbonate | 4.9 |
| Control- contact lens case only | 0 |

Comparative Example

This comparative example is a duplication of Example No. 4 (without binder) of U.S. Pat. No. 5,830,526. To 6.94 g deionized water was added rose bengal disodium salt. A piece (0.5 g) of Walkisoft I1(G409L nonwoven material (75 g) was saturated with the solution and placed between two glass plates under pressure to give a material that weighed 0.75 g (150% pick up). This material was dried at 150° C. in a forced-air oven for 90 seconds.

Then, the material was placed under 50 g/cm$^2$ pressure onto a piece of white paper that had been saturated with 95% by volume ethanol/5% by volume water solution. After 5 seconds, the material was removed from the paper. A bright pink spot was observed, indicating leaching of the dye from the Walkisoft material under these conditions. The delta E value was determined to be 61.1.

The results of this experiment indicate that that the dyed substrates, without binder, investigated and described in U.S. Pat. No. 5,830,526, while possessing dark activity, as described in the example, significantly colorize articles with which they come in contact.

It will be appreciated by those skilled in the art that the method of the present invention will make it possible to inhibit microorganism growth in or on virus-laden, bacteria-laden, or fungi-laden articles or surfaces in the dark as well as in the light. Other viruses, bacteria, and fungi can be similarly tested using the methods of this invention without undue experimentation.

It will be readily understood by those skilled in the art that the foregoing description has been for purposes of illustration only and that a variety of embodiments can be envisioned without departing from the scope of the invention. Therefore, it is intended that the invention not be limited except by the claims. The entirety of each patent, patent document, and publication is incorporated herein by reference as if each was individually incorporated.

What is claimed is:

1. A method of providing an antimicrobial surface, the method comprising combining one or more polymers with one or more photosensitizers to form a surface comprising a hardened polymer composition comprising one or more polymers and one or more photosensitizers, at least one of which is a xanthene photosensitizer, in an amount such that the hardened polymer composition possesses antimicrobial activity in the light and the dark and does not visually colorize white test paper saturated with a 95% by volume ethanol/5% by volume water solution and placed in contact with the hardened polymer composition comprising the one or more photosensitizers under 50-grams/cm$^2$ pressure for 5 minutes;

wherein at least one of the xanthene photosensitizers has the following formula:

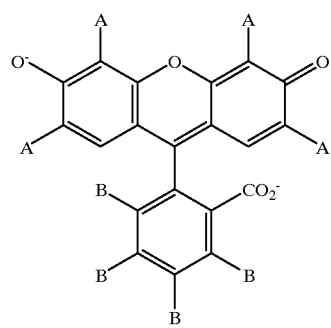

wherein the negative electric charges are balanced independently with the cations Na$^+$, K$^+$, Li$^+$, H$^+$, or substituted ammonium; each A independently represents hydrogen, chlorine, bromine, or iodine; and each B independently represents hydrogen, chlorine, bromine, or iodine.

2. The method of claim 1 wherein the photosensitizer is selected from the group of rose bengal, erythrosin, eosin yellowish, fluorescein, and mixtures thereof.

3. The method of claim 1 wherein the hardened polymer composition is formed from a film-forming composition.

4. The method of claim 1 wherein the hardened polymer composition further comprises a non-photosensitizer antimicrobial agent.

5. The method of claim 1 wherein the hardened polymer composition is in the form of a coating, self-supporting film, or shaped article.

6. The method of claim 1 wherein the photosensitizer is present in the hardened polymer composition in an amount of about 0.01 wt-% to about 10 wt-% based on the dry polymer weight.

7. The method of claim 1 wherein the hardened polymer composition limits the presence of at least one species of virus, at least one species of bacterium, at least one species of fungus, or a combination thereof.

8. The method of claim 7 wherein the hardened polymer composition demonstrates at least about 50% reduction in the amount of at least one species of virus detected on a surface of the hardened polymer composition relative to the same hardened polymer without the one or more photosensitizers under the same conditions.

9. The method of claim 7 wherein the hardened polymer composition demonstrates at least about 40% reduction in the amount of at least one species of fungus or bacterium detected on a surface of the hardened polymer composition relative to the same hardened polymer without the one or more photosensitizers under the same conditions.

10. The method of claim 1 wherein the $\Delta E$ value between a control portion of the test paper and a portion contacted with the hardened polymer composition is no greater than about 2.0.

11. A method of providing an antimicrobial surface, the method comprising combining one or more polymers with one or more photosensitizers to form a surface comprising a hardened polymer composition comprising one or more non-cellulosic polymers and one or more non-covalently bound xanthene photosensitizers in an amount such that the hardened polymer composition possesses antimicrobial activity in the light and the dark and does not visually colorize white test paper saturated with a 95% by volume ethanol/5% by volume water solution and placed in contact with the hardened polymer composition comprising the one or more photosensitizers under 50-grams/cm² pressure for 5 minutes;

wherein at least one of the xanthene photosensitizers has the following formula:

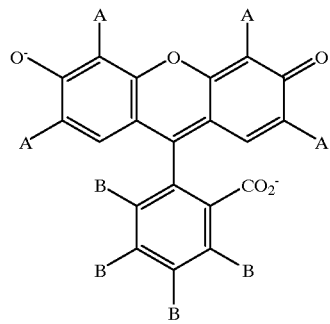

wherein the negative electric charges are balanced independently with the cations $Na^+$, $K^+$, $Li^+$, $H^+$, or substituted ammonium; each A independently represents hydrogen, chlorine, bromine, or iodine; and each B independently represents hydrogen, chlorine, bromine, or iodine.

12. The method of claim 11 wherein the $\Delta E$ value between a control portion of the test paper and a portion contacted with the hardened polymer composition is no greater than about 2.0.

13. A method of limiting the presence of a microorganism, the method comprising contacting the microorganism with a hardened polymer composition comprising one or more polymers and one or more photosensitizers, at least one of which is a xanthene photosensitizer, in an amount such that the hardened polymer composition possesses antimicrobial activity in the light and the dark and does not visually colorize white test paper saturated with a 95% by volume ethanol/5% by volume water solution and placed in contact with the hardened polymer composition comprising the one or more photosensitizers under 50-gram/cm² pressure for 5 minutes;

wherein at least one of the xanthene photosensitizers has the following formula:

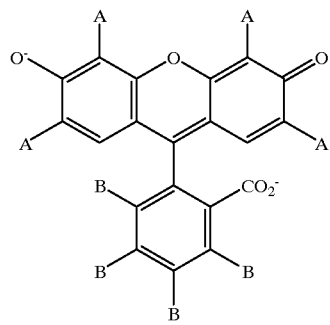

wherein the negative electric charges are balanced independently with the cations $Na^+$, $K^+$, $Li^+$, $H^+$, or substituted ammonium; each A independently represents hydrogen, chlorine, bromine, or iodine; and each B independently represents hydrogen, chlorine, bromine, or iodine.

14. The method of claim 13 wherein the $\Delta E$ value between a control portion of the test paper and a portion contacted with the hardened polymer composition is no greater than about 2.0.

15. The method of claim 13 wherein the photosensitizer is present in the hardened polymer composition in an amount of about 0.01 wt-% to about 10 wt-%, based on the dry polymer weight.

16. The method of claim 13 wherein the hardened polymer composition limits-the presence of at least one species of virus, at least one species of bacterium, at least one species of fungus, or a combination thereof.

17. The method of claim 16 wherein the hardened polymer composition demonstrates at least about 50% reduction in the amount of at least one species of virus detected on a surface of the hardened polymer composition relative to the same hardened polymer without the one or more photosensitizers under the same conditions.

18. The method of claim 16 wherein the hardened polymer composition demonstrates at least about 40% reduction in the amount of at least one species of fungus or bacterium detected on a surface of the hardened polymer composition relative to the same hardened polymer without the one or more photosensitizers under the same conditions.

19. A method of limiting the presence of a microorganism, the method comprising contacting the microorganism with a hardened polymer composition comprising one or more non-cellulosic polymers and one or more non-covalently bound photosensitizers of the formula:

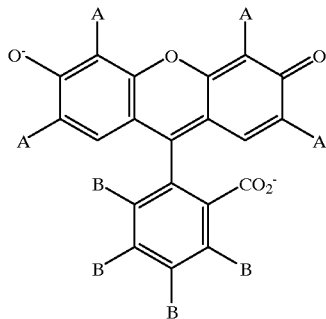

wherein the negative electric charges are balanced independently with the cations $Na^{30}$, $K^+$, $Li^+$, $H^+$, or substituted ammonium, each A independently represents hydrogen, chlorine, bromine, or iodine; and each B independently represents hydrogen, chlorine, bromine, or iodine; wherein the hardened polymer composition possesses antimicrobial activity in the light and the dark and does not visually colorize white test paper saturated with a 95%/o by volume ethanol/5% by volume water solution and placed in contact with the hardened polymer composition comprising the one or more photosensitizers under 50-grams/$cm^2$ pressure for 5 minutes.

20. The method of claim 19 wherein the $\Delta E$, value between a control portion of the test paper and a portion contacted with the hardened polymer composition is no greater than about 2.0.

21. The method of claim 19 wherein the photosensitizer is selected from the group of rose bengal, erythrosin, eosin yellowish, fluorescein, and mixtures thereof.

22. The method of claim 19 wherein the hardened polymer composition is formed from a film-forming composition.

23. The method of claim 19 wherein the hardened polymer composition further comprises a non-photosensitizer antimicrobial agent.

24. The method of claim 19 wherein the hardened polymer composition is in the form of a coating, self-supporting film, or shaped article.

25. An article comprising a hardened polymer composition comprising one or more polymers and one or more photosensitizers, at least one of which is a xanthene photosensitizer, wherein the hardened polymer composition possesses antimicrobial activity in the light and the dark and does not visually colorize white test paper saturated with a 95% by volume ethanol/5% by volume water solution and placed in contact with the hardened polymer composition comprising the one or more photosensitizers under 50-grams/$cm^2$ pressure for 5 minutes; wherein at least one of the xanthene photosensitizers has the following formula:

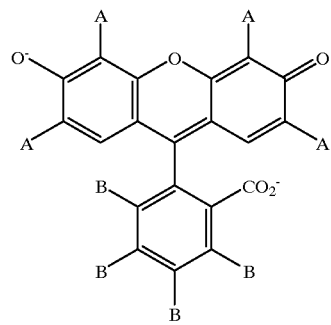

wherein the negative electric charges are balanced independently with the cations $Na^+$, $K^+$, $Li^+$, $H^+$, or substituted ammonium; each A independently represents hydrogen, chlorine, bromine, or iodine; and each B independently represents hydrogen, chlorine, bromine, or iodine.

26. The article of claim 25 wherein the $\Delta E$ value between a control portion of the test paper and a portion contacted with the hardened polymer composition is no greater than about 2.0.

27. The article of claim 26 wherein the photosensitizer is selected from the group of rose bengal, erythrosin, eosin yellowish, fluorescein, and mixtures thereof.

28. The article of claim 26 wherein the hardened polymer composition is in the form of a coating, self-supporting film, or shaped article.

29. The article of claim 26 which is a surgical drape, surgical face mask, dental appliance, cosmetic applicator, sponge, contact lens, contact lens case, catheter, hospital gown, surgical glove, stethoscope, or equipment cover.

30. The article of claim 26 wherein the polymer is a non-cellulosic polymer.

31. The article of claim 26 wherein the one or more photosensitizers is non-covalently bound.

32. An article comprising a hardened polymer composition comprising one or more non-cellulosic polymers and one or more non-covalently bound photosensitizers of the formula:

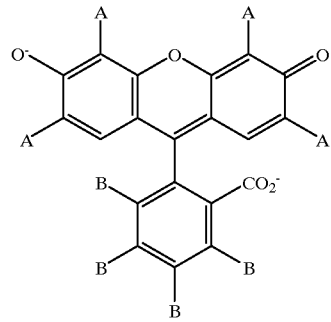

wherein the negative electric charges are balanced independently with the cations $Na^+$, $K^+$, $Li^+$, $H^+$, or substituted ammonium; each A independently represents hydrogen, chlorine, bromine, or iodine; and each B independently represents hydrogen, chlorine, bromine, or iodine; wherein the hardened polymer composition possesses antimicrobial activity in the light and the dark and does not visually colorize white test paper saturated with a 95% by volume ethanol/5% water solution and placed in contact with the hardened polymer composition comprising the one or more photosensitizers under a 50-grams/cm² pressure for 5 minutes.

33. A stethoscope comprising a hardened polymer composition comprising one or more polymers and one or more photosensitizers wherein the hardened polymer composition possesses antimicrobial activity in the light and the dark and does not visually colorize white test paper saturated with a 95% by volume ethanol/5% by volume water solution and placed in contact with the hardened polymer composition comprising the one or more photosensitizers under 50-grams/cm² pressure for 5 minutes.

34. The contact lens case to claim 1 wherein at least one of the photosensitizers has the following formula:

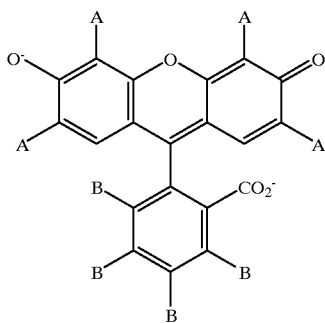

wherein the negative electric charges are balanced independently with the cations Na⁺, K⁺, Li⁺, H⁺, or substituted ammonium; each A independently represents hydrogen, chlorine, bromine, or iodine; and each B independently represents hydrogen, chlorine, bromine, or iodine.

35. The stethoscope of claim 33 wherein at least one of the photosensitizers has the following formula:

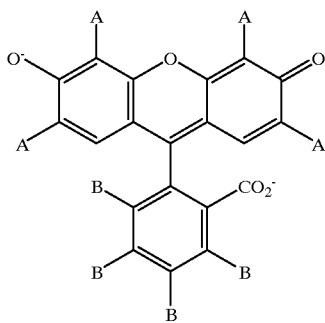

wherein the negative electric charges are balanced independently with the cations Na⁺, K⁺, Li⁺, H⁺, or substituted ammonium; each A independently represents hydrogen, chlorine, bromine, or iodine; and each B independently represents hydrogen, chlorine, bromine, or iodine.

36. The stethoscope of claim 33 wherein the hardened polymer composition is formed from a film-forming composition.

37. The stethoscope of claim 33 wherein the hardened polymer composition further comprises a non-photosensitizer antimicrobial agent.

38. The stethoscope of claim 33 wherein the hardened polymer composition is in the form of a coating, self-supporting film, or shaped article.

39. The stethoscope of claim 33 wherein the photosensitizer is present in the hardened polymer composition in an amount of about 0.01 wt-% to about 10 wt-%, based on the dry polymer weight.

40. The stethoscope of claim 33 wherein the hardened polymer composition limits the presence of at least one species of virus, at least one species of bacterium, at least one species of fungus, or a combination thereof.

41. The stethoscope of claim 33 wherein the hardened polymer composition demonstrates at least about 50% reduction in the amount of at least one species of virus detected on a surface of the hardened polymer composition relative to the same hardened polymer without the one or more photosensitizers under the same conditions.

42. The stethoscope of claim 33 wherein the hardened polymer composition demonstrates at least about 40% reduction in the amount of at least one species of fungus or bacterium detected on a surface of the hardened polymer composition relative to the same hardened polymer without the one or more photosensitizers under the same conditions.

43. The stethoscope of claim 33 wherein the ΔE value between a control portion of the test paper and a portion contacted with the hardened polymer composition is no greater than about 2.0.

44. The method of claim 1 wherein the hardened polymer composition comprising one or more polymers and one or more photosensitizers, at least one of which is a xanthene photosensitizer, comprises one or more polymers and one or more non-covalently and non-ionically bound photosensitizers.

45. The method of claim 11 wherein one or more non-covalently bound xanthene photosensitizers are also non-ionically bound.

46. The method of claim 13 wherein the hardened polymer composition comprising one or more polymers and one or more photosensitizers, at least one of which is a xanthene photosensitizer, comprises one or more polymers and one or more non-covalently and non-ionically bound photosensitizers.

47. The method of claim 19 wherein the one or more non-covalently bound photosensitizers are also non-ionically bound.

48. The article of claim 26 wherein the hardened polymer composition comprising one or more polymers and one or more photosensitizers, at least one of which is a xanthene photosensitizer, comprises one or more polymers and one or more non-covalently and non-ionically bound photosensitizers.

49. The article of claim 33 wherein the one or more non-covalently bound photosensitizers are also non-ionically bound.

50. The stethoscope of claim 33 wherein the hardened polymer composition comprising one or more polymers and one or more photosensitizers comprises one or more polymers and one or more non-covalently and non-ionically bound photosensitizers.

* * * * *

UNITED STATES PATENT AND TRADEMARK OFFICE
CERTIFICATE OF CORRECTION

PATENT NO. : 6,420,455 B1
DATED : July 16, 2002
INVENTOR(S) : Landgrebe, Kevin D.

It is certified that error appears in the above-identified patent and that said Letters Patent is hereby corrected as shown below:

Column 1,
Line 20, delete "no".

Column 2,
Line 57, delete "5,820,526" and insert in place thereof -- 5,830,526 --.

Column 3,
Line 21, delete "Scheffer" and insert in place thereof -- Tseng --.

Column 7,
Line 10, after "polymer" insert -- by casting from a solvent --.

Column 9,
Line 35, delete "Entertococcus" and insert in place thereof -- Enterococcus --.
Line 36, delete "aeruiginosa" and insert in place thereof -- aeruginosa --.
Line 41, delete "Entertococcus" and insert in place thereof -- Enterococcus --; delete "Streptococcuts" and insert in place thereof -- Streptococcus --.

Column 10,
Line 32, delete "." and insert place thereof -- , --.

Column 13,
Line 39, delete "For" and insert in place thereof -- for --.

Column 14,
Line 62, delete "." and insert in place thereof -- , --.

Column 16,
Line 24, delete "NIAII)" and insert in place thereof -- NIAID --.

UNITED STATES PATENT AND TRADEMARK OFFICE
CERTIFICATE OF CORRECTION

PATENT NO.    : 6,420,455 B1
DATED         : July 16, 2002
INVENTOR(S)   : Landgrebe, Kevin D.

It is certified that error appears in the above-identified patent and that said Letters Patent is hereby corrected as shown below:

<u>Columns 17-18, Table 2,</u>
Under the column identified as "Percent Reduction [dark]", delete "64" and insert in place thereof -- 98 --.

Under the column identified as "Percent Reduction [room light]", delete "5" and insert in place thereof  -- 39 --; delete "69" and insert in place thereof -- 36 --.

<u>Columns 19-20, Table 4,</u>
Under the column identified as "Percent Reduction [room light]", delete "94" and insert in place thereof -- 99 --.

<u>Column 24,</u>
Line 2, delete "I1(G409L" and insert in place thereof -- FG409L --.

<u>Column 27,</u>
Line 35, delete "$Na^{30}$" and insert in place thereof -- $Na^+$ --.

<u>Column 29,</u>
Line 53, delete "arc" and insert in place thereof -- are --.

Signed and Sealed this

Thirteenth Day of May, 2003

JAMES E. ROGAN
*Director of the United States Patent and Trademark Office*